US009405869B2

(12) United States Patent
Akutagawa (10) Patent No.: US 9,405,869 B2
(45) Date of Patent: Aug. 2, 2016

(54) RUBBER PRODUCT ELASTIC RESPONSE PERFORMANCE PREDICTION METHOD, DESIGN METHOD, AND ELASTIC RESPONSE PERFORMANCE PREDICTION APPARATUS (75) Inventor: Keizo Akutagawa, Kodaira (JP)

(73) Assignee: BRIDGESTONE CORPORATION, Tokyo (JP)

(*) Notice: Subject to any disclaimer, the term of this patent is extended or adjusted under 35 U.S.C. 154(b) by 207 days.

(21) Appl. No.: 13/877,607

(22) PCT Filed: Oct. 4, 2011

(86) PCT No.: PCT/JP2011/072887
§ 371 (c)(1),
(2), (4) Date: Apr. 3, 2013

(87) PCT Pub. No.: WO2012/046740
PCT Pub. Date: Apr. 12, 2012

(65) Prior Publication Data
US 2013/0211802 A1 Aug. 15, 2013

(30) Foreign Application Priority Data
Oct. 5, 2010 (JP) ................................. 2010-225985

(51) Int. Cl.
G06F 17/50 (2006.01)
G01N 33/44 (2006.01)
(52) U.S. Cl.
CPC .......... *G06F 17/5018* (2013.01); *G01N 33/445* (2013.01); *G01N 2203/0092* (2013.01); *G01N 2203/0216* (2013.01)

(58) Field of Classification Search
CPC ............ G06F 17/5018; G06F 17/5009; G06F 2217/16
USPC ...................................................... 703/2, 6, 7
See application file for complete search history.

(56) References Cited

U.S. PATENT DOCUMENTS

2010/0305910 A1* 12/2010 Yilbas .................... B23K 31/12
703/2

FOREIGN PATENT DOCUMENTS

JP     2007-265266 A   10/2007
JP     4299735 B2       7/2009

OTHER PUBLICATIONS

Kawabata et al. "Strain Energy Density Functions of Rubber Vulcanizates from Biaxial Extension", Department of Polymer Chemistry, Kyoto University, Kyoto 606, Japan, Received Jul. 7, 1976.*
DeVoe "Thermodynamics and Chemistry", C 2001 by Prentice-Hall, Upper Saddle, NJ07458, pp. 89-90.*
Deam et al. "The Theory of Rubbert Elasticity", Phil. Trans. R. Soc. Lond. A 1976 280, published Jan. 8, 1976, pp. 317-353.*
(Continued)

Primary Examiner — Omar Fernandez Rivas
Assistant Examiner — Shiuh-Huei Ku
(74) Attorney, Agent, or Firm — Sughrue Mion, PLLC (57) ABSTRACT An elastic response performance prediction method that employs a finite element analysis method to predict an elastic response performance expressing deformation behavior of a rubber product. The elastic response performance of the rubber product is predicted by employing a constitutive equation that expresses temperature and strain dependence of strain energy in the rubber product expressed using a parameter representing intermolecular interaction.

6 Claims, 4 Drawing Sheets (56) References Cited

OTHER PUBLICATIONS

A.D. Drozdov, "A model for the mechanical response of composites with thermoplastic-elastomer metrics", Composites Science and Technology, 2006, pp. 2648-2663, vol. 66, No. 15.
International Search Report for PCT/JP2011/072887 dated Nov. 8, 2011.
"Theory of constellation elasticity of chain molecules", Science in China (Series B), Feb. 28, 2001, pp. 78-87.
"Mechanical behavior of amorphous high polymer due to shear deformation", Applied Mathematics and Mechanics, Oct. 31, 2004, pp. 997-1006.
"Finite element modeling of rubber mount and its static elastic characteristic simulation", Automotive Engineering, Dec. 31, 2002, pp. 480-485, vol. 24, No. 6.
Chinese Office Action, dated May 28, 2014, issued in corresponding Chinese Patent Application No. 201180048359.0.
Michael Kaliske et al., "On damage modelling for elastic and viscoelastic materials at large strain", Computers & Structures, 2001, vol. 79, pp. 2133-2141.

* cited by examiner

RUBBER PRODUCT ELASTIC RESPONSE PERFORMANCE PREDICTION METHOD, DESIGN METHOD, AND ELASTIC RESPONSE PERFORMANCE PREDICTION APPARATUS

CROSS REFERENCE TO RELATED APPLICATIONS

This application is a National Stage of International Application No. PCT/JP2011/072887, filed on Oct. 4, 2011, which claims priority from Japanese Patent Application No. 2010-225985, filed on Oct. 5, 2010, the contents of all of which are incorporated herein by reference in their entirety.

TECHNICAL FIELD

The present invention relates to an elastic response performance prediction method and design method for a rubber product, and to an elastic response performance prediction apparatus. In particular the present invention relates to a prediction method that employs a Finite Element Analysis (FEA) method to predict an elastic response performance of a rubber product, to a rubber product design method employing the prediction method, and to an elastic response performance prediction apparatus thereof.

BACKGROUND ART

When designing a rubber product, methods that employ 3-D Finite Element Analysis (FEA) methods to predict the elastic response thereof, and that employ such analysis and simulation results have already been implemented for tens of years. Energy constitutive equations are employed in FEA computation and in the analysis reflect a stress-strain relationship of a rubber material, migrate linear elasticity equations into Mooney-Rivlin equations, and recently non-linear constitutive equations are being introduced for regions of large deformation in such energy constitutive equations.

Moreover, recently with regard to such a rubber material constitutive equation, under the principles of lattice deformation theory developed with molecular statistical thermodynamics based on the extension of rubber molecular chains, there is a proposal for a constitutive equation that is capable of expressing temperature dependence, an important factor in the design of a lot of industrial rubber materials, such as tires, using a parameter with a physical meaning (Japanese Patent No. 4299735).

A summary of such a constitutive equation follows.

First, tensional stress in rubber is expressed by a shear elastic modulus G and a tension direction extension ratio $\lambda$ using the following Equation (1).

$$\sigma = 2G\left(\lambda - \frac{1}{\lambda^2}\right) \quad (1)$$

Moreover, the shear elastic modulus G of rubber is computable, as shown in the following Equation (2), by differentiating the Helmholz free energy A of statistical thermodynamics with respect to $I_1$.

$$\frac{G}{2} = \frac{\partial A}{\partial I_1} \quad (2)$$

The average energy $\overline{A}_\alpha$ of a system in a thermodynamic equilibrium state is expressed by the following Equation (3).

$$\overline{A}_\alpha = \frac{1}{Z}\sum A_\alpha e^{-\beta A_\alpha} = -\left(\frac{\partial \log Z}{\partial \beta}\right)_{[\Gamma]} \quad (3)$$

$\beta$ here is equivalent to $1/(k\Delta T)$, wherein k represents the Helmholz constant and $\Delta T$ represents the difference from a polymer glass transition temperature $T_g$ to the measured temperature T. Moreover, $A_\alpha$ represents the energy level. Z is a distribution function for standardizing the energy of the system, and is expressed by the following Equation (4).

$$Z = \sum_\alpha e^{-\beta A_\alpha} = \sum_\alpha e^{-\beta(U_\alpha - TS_\alpha)} \quad (4)$$

Here, as expressed in the following Equation (5), $U_\alpha$ can be assumed to be equivalent to Hamiltonian H from a statistical thermodynamic perspective.

$$U_\alpha = H \text{ (Temp, Constraints)} \quad (5)$$

Wherein, the Hamiltonian H is expressed as a function of temperature conditions and constraint conditions defining microstates in statistical thermodynamics.

Two states are set, a low temperature state and a high temperature state, as a model expressing temperature dependence of rubber molecules, and state numbers of rubber molecule called $r_1$ and $r_2$ are distributed in strain energy fields called $I_{1a}$ and $I_{1b}$. This can be represented by the following Equation (6) when this is applied to express all of the states as a function.

$$Z = \sum_\alpha e^{-\beta A_\alpha} = \sum_\alpha e^{-\beta(U_\alpha - TS_\alpha)} = \quad (6)$$

$$e^{\beta TS}\left(e^{-\frac{-I_{1a}-I_{1b}-\kappa}{k\Delta T}} + e^{-\frac{-I_{1a}+I_{1b}}{k\Delta T}} + e^{-\frac{I_{1a}-I_{1b}}{k\Delta T}} + e^{-\frac{I_{1a}+I_{1b}-\kappa}{k\Delta T}}\right)$$

$$= 2e^{\beta TS}\left[e^{\frac{\kappa}{k\Delta T}}\cosh\left(\frac{I_{1a}+I_{1b}}{k\Delta T}\right) + \cosh\left(\frac{I_{1a}-I_{1b}}{k\Delta T}\right)\right]$$

Wherein $\kappa$ represents molecular recoil energy. Two states of different rubber molecule energy states are represented by $r_1=-1$, $r_2=1$, and the statistical thermodynamic average thereof is represented by $<r_1 \cdot r_2>$. This product expresses the two extreme end energy states, and when this product is +1 this represents rubber molecules being in the same state, and when this product is −1 this represents rubber molecules being in different states. Assuming that the strain energy field contribution is equal for all of the molecules, then by making $I_1 = I_{1a} = I_{1b}$, Equation (6) above can be expressed by the following Equation (7).

$$Z = \sum_\alpha e^{-\beta A_\alpha} = 2e^{\beta TS}\left[e^{\frac{\kappa}{k\Delta T}}\cosh(2\beta \cdot I_1) + 1\right] \quad (7)$$

Substituting Equation (7) in above Equation (3) expresses the rubber elastic modulus G by the following Equation (9).

$$\bar{A}_\alpha = \frac{1}{Z}\sum A_\alpha e^{-\beta A_\alpha} = -\left(\frac{\partial \log Z}{\partial \beta}\right)_{(\Gamma)} = -\frac{\partial}{\partial \beta}\left[e^{\frac{\kappa}{k\Delta T}}\cosh(2\beta \cdot I_1) + 1\right] - T \cdot S \tag{8}$$

$$\frac{G}{2} = \tag{9}$$

$$\frac{\partial \bar{A}_\alpha}{\partial I_1} = \frac{\partial U}{\partial I_1} - T \cdot \frac{\partial S}{\partial I_1} = -\frac{\partial}{\partial \beta \partial I_1}\left[e^{\frac{x}{k\Delta T}}\cosh(2\beta \cdot I_1) + 1\right] - T \cdot \frac{\partial S}{\partial I_1}$$

Considering a stretched molecule, the second term of the entropy term in Equation (9) is expressed using a Langevin function by the following Equation (10).

$$T \cdot \frac{\partial S}{\partial I_1} = -vRT\left[\frac{1}{2} + \frac{3}{50n}\left(3I_1 - \frac{2}{\lambda}\right) + \frac{297}{6125n^2}\left(5I_1^2 - 4I_2 - 4\frac{I_1}{\lambda}\right)\right] \tag{10}$$

Wherein n is defined as the number of links of a statistical molecule chain between cross-linked points.

Accordingly, Japanese Patent No. 4299735 proposes a constitutive equation that is capable of representing temperature dependence and employs a parameter with physical meaning.

Figure 6:
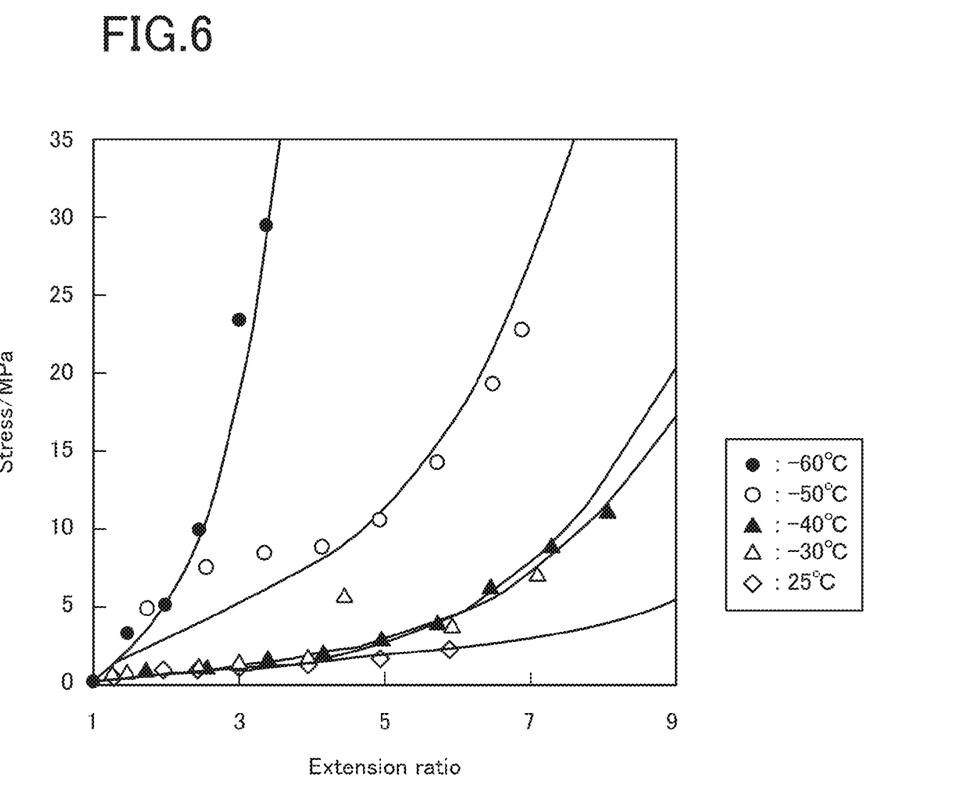
FIG. 6 is a graph illustrating prediction values related to temperature dependence of a stress-strain curve for rubber using related technology and observed values.

Moreover, as illustrated in FIG. 6, a strain energy function (solid line) disclosed in Japanese Patent No. 4299735 is able to replicate test values (plots) over a wide range of extension ratios and temperature regions.

DISCLOSURE OF INVENTION

Technical Problem

However, in the strain energy function disclosed in Japanese Patent No. 4299735, since test values and theoretical values diverge in regions of low extension ratio under low temperature conditions, this leads to the issue that the elastic response performance of a rubber product cannot be predicted with good precision under low temperature conditions.

The present invention is directed towards solving the above issue, and an object thereof is to provide an elastic response performance prediction method, a rubber product design method and an elastic response performance prediction apparatus that are capable of raising prediction precision of the elastic response performance of rubber products even under low temperature conditions.

Solution to Problem

In order to achieve the above objective, a first aspect of the present invention is an elastic response performance prediction method that predicts an elastic response performance expressing deformation behavior of a rubber product by predicting the elastic response performance of the rubber product by employing a constitutive equation that expresses temperature and strain dependence of strain energy in the rubber product using a parameter representing intermolecular interaction.

A second aspect of the present invention is an elastic response performance prediction apparatus that predicts elastic response performance expressing deformation behavior of a rubber product by predicting the elastic response performance of the rubber product by employing a constitutive equation that expresses temperature and strain dependence of strain energy in the rubber product expressed using a parameter representing intermolecular interaction.

According to the first aspect and the second aspect of the present invention, when a filler based rubber is observed by observation at the micro-level, in a diffuse deformation region of a rubber product containing a low extension ratio region (for example an extension ratio of 100% or less), a constitutive equation is employed that expresses temperature and strain dependence of strain energy and employs a parameter representing intermolecular interaction, and the elastic response performance of the rubber product is predicted. Accordingly, elastic response performance can be predicted with good precision for low extension ratio regions under low temperature conditions. Thus, for rubber composite products made from filler based rubber materials which are particularly important in practice, the elastic response performance of the rubber product can be predicted with good precision using temperature and strain dependent parameters with a physical meaning and under low temperature conditions, with this being important in the design of many industrial rubber products.

According to a third aspect of the present invention, the constitutive equation is the following Equation (I):

$$\Delta A = (U_1 - TS_1) + p(V_1 - V_0) - (U_0 - TS_0) \tag{I}$$

Wherein A represents Helmholz free energy, $U_0$ represents internal energy in a non-deformed state and $U_1$ represents internal energy in a deformed state. p represents pressure, $V_0$ represents volume in a non-deformed state, $V_1$ represents volume in a deformed state and T represents absolute temperature. $S_0$ represents entropy in a non-deformed state, and $S_1$ represents entropy in a deformed state. Each of the terms of Equation (I) is respectively expressed by the following Equations (II) to (IV):

$$U_1 - T \cdot S_1 = \frac{e^{\beta' \cdot \kappa}\{\kappa \cosh(2\beta'(I_1' - 3)) + 2(I_1' - 3) \cdot \sinh(2\beta'(I_1' - 3))\}}{e^{\beta'\kappa}\cosh(2\beta'(I_1' - 3)) + 1} - \frac{N}{\beta} \cdot \left\{\frac{1}{2}I_1 + \frac{3}{100n}(3I_1^2 - 4I_2) + \frac{99}{12250n}(5I_1^3 - 12I_1 I_2)\right\} \tag{II}$$

$$p(V_1 - V_0) = B \cdot (V_1 - V_0) = B\left(I_3^{\frac{1}{2}} - 1\right)^2 - \frac{1}{\beta'}\{\ln[1 + e^{\beta' \cdot \kappa}\cosh(2\beta'(I_1' - 3))] - \ln[1 + e^{\beta' \cdot \kappa}]\} \tag{III}$$

$$U_0 - T \cdot S_0 = \frac{\kappa \cdot e^{\beta' \cdot \kappa}}{e^{\beta' \cdot \kappa} + 1} + \frac{N}{\beta}\left(\frac{3}{2} + \frac{45}{100n} + \frac{2673}{12250n^2}\right) \tag{IV}$$

Wherein: $I_1$, $I_2$, and $I_3$ are expressed as functions of three extension ratios of deformation $\lambda_1$, $\lambda_2$ and $\lambda_3$ in xyz directions in three dimensional axes of rubber by $I_1 = \lambda_1^2 + \lambda_2^2 + \lambda_3^2$, $I_2 = \lambda_1^2 \cdot \lambda_2^2 + \lambda_2^2 \cdot \lambda_3^2 \cdot \lambda_1^2$, and $I_3 = \lambda_1^2 \cdot \lambda_2^2 \cdot \lambda_3^2$. n represents a number of links between cross-linked points in a statistical molecule chain and κ expresses an intermolecular interaction energy coefficient. $\beta = 1/RT$ and $\beta' = 1/R(T - T_g)$ wherein R is a gas constant and $T_g$ is a glass transition temperature, and $I_1'$ is expressed using a local interaction function $\lambda_{micro}$ as a parameter expressing the intermolecular interaction by the following Equation (V):

$$I_1' = \lambda_{micro}^2(\lambda_1^2 + \lambda_2^2 + \lambda_3^2) = \lambda_{micro}^2 \cdot I_1 \tag{V}$$

A fourth aspect of the present invention is an elastic response performance prediction method that predicts elastic response performance expressing deformation behavior of a rubber product by predicting the elastic response performance of the rubber product by employing a constitutive equation that expresses temperature and strain dependence of an elastic modulus of the rubber product expressed using a parameter representing intermolecular interaction.

A fifth aspect of the present invention is an elastic response performance prediction apparatus that predicts elastic response performance expressing deformation behavior of a rubber product by predicting the elastic response performance of the rubber product by employing a constitutive equation that expresses temperature and strain dependence of an elastic modulus of the rubber product expressed using a parameter representing intermolecular interaction.

According to the fourth aspect and the fifth aspect of the present invention, when a filler based rubber is observed by observation at the micro-level, in a diffuse deformation region of a rubber product containing a low extension ratio region (for example an extension ratio of 100% or less), a constitutive equation is employed that expresses temperature and strain dependence of an elastic modulus and employs a parameter representing intermolecular interaction, and the elastic response performance of the rubber product is predicted. Accordingly, elastic response performance can be predicted with good precision for low extension ratio regions under low temperature conditions. Thus, for rubber composite products made from filler based rubber materials which are particularly important in practice, the elastic response performance of the rubber product can be predicted with good precision using temperature and strain dependent parameters with a physical meaning and under low temperature conditions, with this being important in the design of many industrial rubber products.

In a sixth aspect of the present invention the constitutive equation is the following Equation (VI):

$$G = \frac{\partial W}{\partial I_1} = \frac{\partial A}{\partial I_1} = \frac{\partial U}{\partial I_1} - T \cdot \frac{\partial S}{\partial I_1} + \frac{\partial pV}{\partial I_1} \quad (VI)$$

Wherein G represents a shear elastic modulus, W represents a strain energy coefficient and A represents Helmholz free energy. U represents internal energy, T represents absolute temperature and S represents entropy. $I_1$ is expressed as a function of three extension ratios of deformation $\lambda_1, \lambda_2$ and $\lambda_3$ in xyz directions in three dimensional axes of rubber by $I_1 = \lambda_1^2 + \lambda_2^2 + \lambda_3^2$. Each of the terms of Equation (VI) is respectively expressed by the following Equation (VII), Equation (VIII), and Equation (IX):

$$\frac{\partial U}{\partial I_1} = \frac{-e^{\beta'\kappa}\left\{\begin{array}{c} 2e^{\beta'\kappa}\sinh(2\beta'(I_1'-3))\cosh(2\beta'(I_1'-3)) + \\ 2(\beta'\kappa+1)\sinh(2\beta'(I_1'-3)) + \\ 4\beta'(I_1'-3)\cosh(2\beta'(I_1'-3)) + 4\beta'(I_1'-3)e^{\beta'\kappa} \end{array}\right\}}{\{e^{\beta'\kappa}\cdot\cosh(2\beta'(I_1'-3))+1\}^2} \quad (VII)$$

$$\frac{\partial S}{\partial I_1} = -vR\left[\frac{1}{2} + \frac{3}{50n}\left(3I_1 - \frac{2}{\lambda}\right) + \frac{297}{6125n^2}\left(5I_1^2 - 4I_3 - 4\frac{I_1}{\lambda}\right)\right] \quad (VIII)$$

$$\frac{\partial pV}{\partial I_1} = \frac{2 \cdot e^{\beta'\kappa} \cdot \cosh(2\beta'(I_1'-3))}{e^{\beta'\kappa} \cdot \cosh(2\beta'(I_1'-3))+1} \quad (IX)$$

Wherein n represents a number of links between the cross-linked points in the statistical molecule chain, κ expresses an intermolecular interaction energy coefficient, ν represents a cross-link density, and λ represents an extension ratio or compression ratio. $\beta' = 1/R(T-T_g)$ wherein R is a gas constant and $T_g$ is a glass transition temperature. $I_2$ is represented by $I_2 = \lambda_1^2 \cdot \lambda_2^2 + \lambda_2^2 \cdot \lambda_3^2 + \lambda_3^2 \cdot \lambda_1^2$. $I_1'$ is expressed using a local interaction function $\lambda_{micro}$ as a parameter expressing the intermolecular interaction by the following Equation (X):

$$I_1' = \lambda_{micro}^2(\lambda_1^2 + \lambda_2^2 + \lambda_3^2) = \lambda_{micro}^2 \cdot I_1 \quad (X)$$

According to a seventh aspect of the present invention, the elastic response performance expressing deformation behavior of the rubber product may be predicted by employing a finite element analysis method.

The present invention, as explained in detail above, predicts the elastic response performance of a rubber product by employing a constitutive equation that expresses the temperature and strain dependence of strain energy in the rubber product, or by employing a constitutive equation that expresses the temperature and strain dependence of an elastic modulus of the rubber product. It is accordingly possible, through necessary simulation, and in particular through simulation of rubber at the micro-level, to design at the micro level an optimum rubber material to achieve the desired properties of the rubber product. A design method for a rubber product can also be provided that is both efficient and has good precision.

Advantageous Effects of Invention

As explained above, according to the elastic response performance prediction method, the rubber product design method and the elastic response performance prediction apparatus of the present invention, an elastic response performance of a rubber product is predicted by employing a constitutive equation that expresses temperature and strain dependence of strain energy using a parameter representing intermolecular interaction, or by employing a constitutive equation that expresses temperature and strain dependence of an elastic modulus. An advantageous effect is accordingly achieved of enabling the elastic response performance to be predicted with good precision under low temperature conditions.

BEST MODE FOR CARRYING OUT THE INVENTION

Detailed explanation follows regarding an exemplary embodiment of the present invention, with reference to the drawings.

Figure 1:
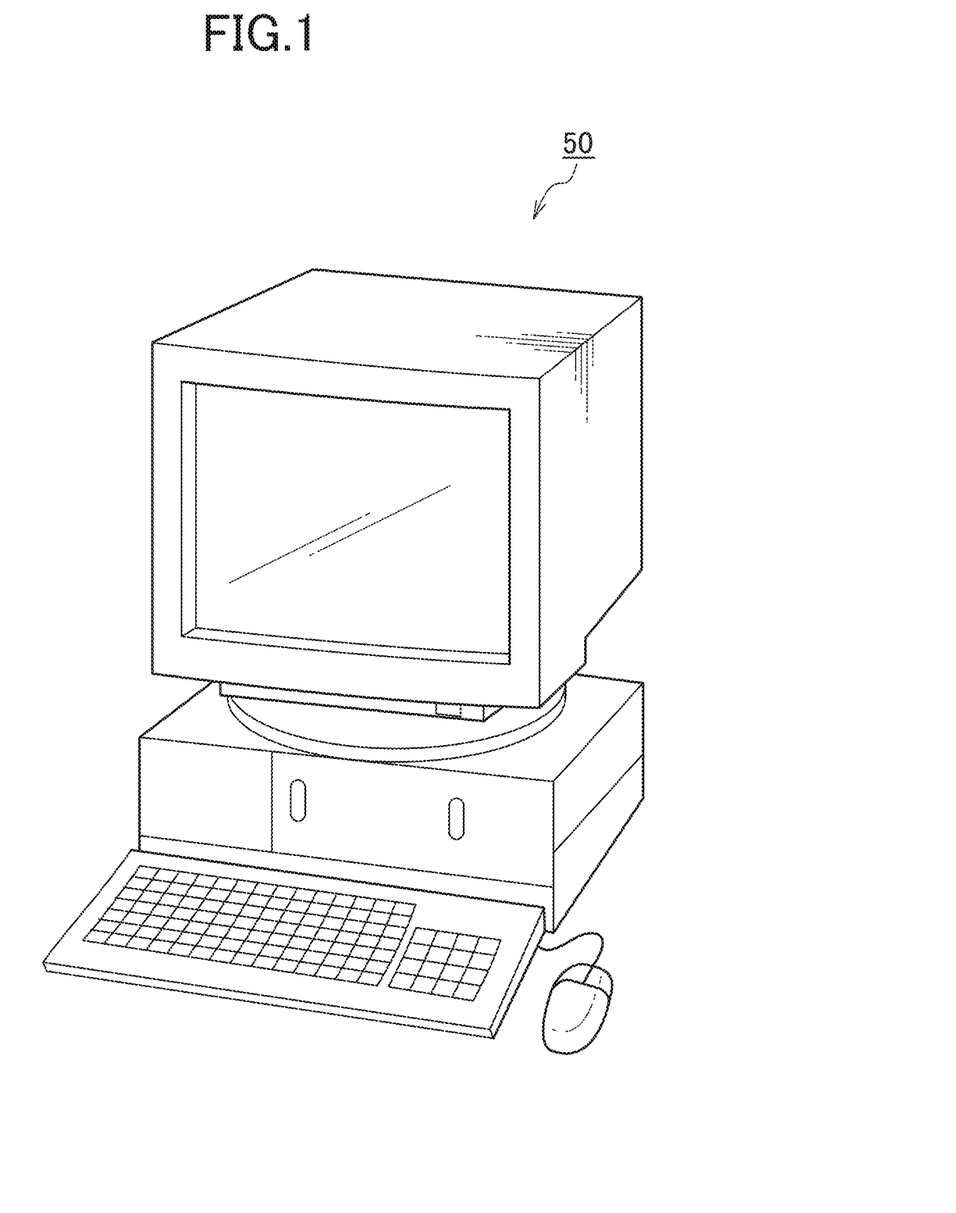
FIG. 1 is a schematic diagram illustrating an elastic response performance prediction apparatus according to an exemplary embodiment of the present invention.

As illustrated in FIG. 1, an elastic response performance prediction apparatus 50 according to a first exemplary embodiment of the present invention is configured by a computer computation processing system that executes processing, described later, with an elastic response performance prediction program in order to execute elastic response performance prediction. Note that such a computer system is, for example, configured with a CPU, ROM, RAM, a hard disk, an input-output terminal, and other required units. The elastic response performance prediction program referred to above is preinstalled on a hard disk or the like.

The elastic response performance prediction method of the first exemplary embodiment of the present invention employs a constitutive equation expressing temperature and strain dependence of strain energy in a rubber material constituting a rubber product, and in particular preferably employs the Equations (I) to (IV) described above, to predict the elastic response performance of the rubber product.

Explanation follows regarding derivation principles of a constitutive equation expressing the temperature and strain dependence of strain energy in a rubber material. In the following, a microstructure model is defined for statistical thermodynamic computation, and a constitutive equation is derived based on this model.

Figure 2:
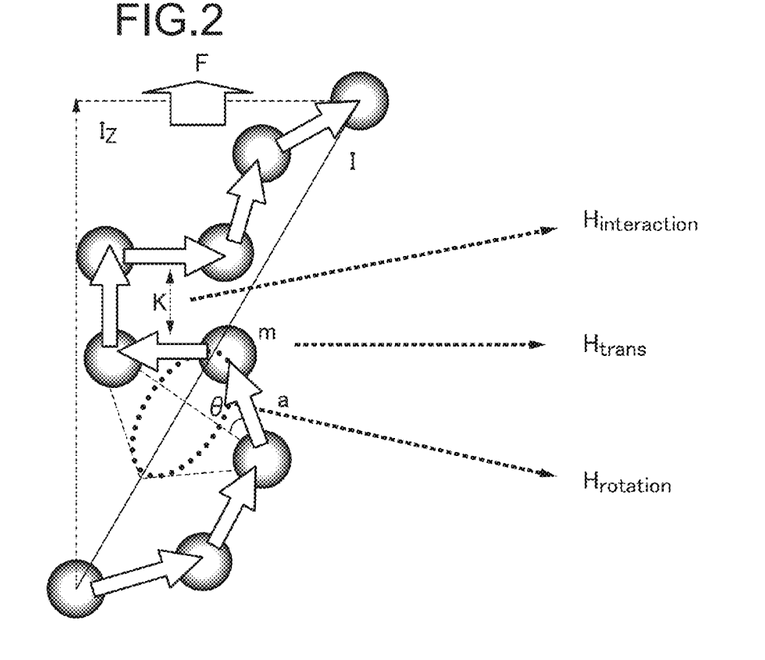
FIG. 2 is an image of a microstructure model for deriving the present constitutive equation.

FIG. 2 illustrates a microstructure model. $H_{int}$ is a Hamiltonian expressing intermolecular or intramolecular interaction, $H_{rot}$ is a Hamiltonian expressing molecular rotation, and $H_{trans}$ is a Hamiltonian expressing molecular translation.

A thermodynamic equation representing this microstructure model can be expressed by the following Equation (11).

$$\Delta A = \Delta U + p\Delta V - T\Delta S = f(\overline{Z}_{int}, \overline{Z}_{rot}, \overline{Z}_{trans}) = g(H_{int}, H_{rot}, H_{trans}) \qquad (11)$$

Wherein: A represents Helmholz free energy, U represents internal energy, and p represents pressure. V represents volume, T represents absolute temperature and S represents entropy. $\overline{Z}_{int}$ represents a distribution function expressing intermolecular or intramolecular interaction, $\overline{Z}_{rot}$ represents a distribution function expressing molecular rotation, and $\overline{Z}_{trans}$ represents a distribution function expressing molecular translation. The Hamiltonians corresponding to each of the molecular motion modes are expressed by the following Equation (12) to Equation (14).

$$H_{interaction} = (r_1 + r_2) \cdot I - \kappa \cdot \delta_{r_1, r_2} \qquad (12)$$

$$H_{trans} = \frac{p^2}{2 \cdot m} + (r_1 + r_2) \cdot I - \kappa \cdot \delta_{r_1, r_2} \qquad (13)$$

$$H_{rotation} = \frac{p_\theta^2}{2 \cdot I_M} + \frac{p_\phi^2}{2 \cdot I_M \cdot \sin^2\theta} - F \cdot a \cdot \cos\theta \qquad (14)$$

Wherein $r_1$ and $r_2$ represent two molecular energy states of intermolecular or intramolecular interaction. When $I_1'$ represents an invariant of intermolecular strain in the microstructure model illustrated in FIG. 2, then $r_1$ and $r_2$ are expressed by either +1 or −1. Strain energy due to deformation represented by $I_1'$ corresponds to the four combinations (−1, −1), (+1, +1), (+1, −1), and (−1, +1). κ is a coefficient expressing the magnitude of interaction energy. δ is a coefficient expressing a state involving interaction energy, and is −1 when two individual molecules are in the same energy state. When the two individual molecules are in the same energy state, κ·δ becomes a minus coefficient, meaning stabilization by the amount of the interaction energy. However, when in different energy states, κ·δ becomes 0, assuming that no interaction occurs. m expresses molecular mass, $P_\theta$ represents momentum expressing an angle of molecular rotation with respect to an axis connecting two molecules together. $P_\phi$ represents momentum expressing molecular rotation with respect to a rotation angle around the axis connecting two molecules together, P represents momentum with respect to a molecule of mass m, and $I_M$ an inertial moment of molecular rotation.

A relationship between a Hamiltonian and a distribution function is expressed by the following Equation (15).

$$Z_\alpha = \Sigma \{e^{\beta \cdot H\alpha}\} \qquad (15)$$

Substituting Hamiltonians corresponding to each of the molecule motion modes into the relationship equation expressed above by Equation (15) gives each of the distribution functions expressed by the following Equation (16) to Equation (18).

$$z_{int} = \sum \{e^{\beta' \cdot (-I_1' - I_1' - \kappa)} + e^{\beta' \cdot (-I_1' + I_1')} + e^{\beta' \cdot (I_1' - I_1')} + e^{\beta' \cdot (I_1' + I_1' - \kappa)}\} \qquad (16)$$

$$z_{rot} = \sum \exp\left\{\beta \cdot \left(\frac{P_\theta^2}{2 \cdot I_M} + \frac{P_\phi^2}{2 \cdot I_M \cdot \sin^2\theta} - F \cdot a \cdot \cos\theta\right)\right\} \qquad (17)$$

$$z_{trans} = \sum \exp\left\{\beta \cdot \left(\frac{P^2}{2m}\right)\right\} + \sum \{e^{\beta' \cdot (-I_1' - I_1' - \kappa)} + e^{\beta' \cdot (-I_1' + I_1')} + e^{\beta' \cdot (I_1' - I_1')} + e^{\beta' \cdot (I_1' + I_1' - \kappa)}\} \qquad (18)$$

Solving the above relationships derives the following Equation (19) to Equation (21).

$$z_{int} = 2\left[e^{\beta'\kappa} \cosh\{2\beta'(I_1' - 3)\} + 1\right] \qquad (19)$$

$$z_{rot} = \frac{2 \cdot I_M}{\beta} \cdot \frac{\sinh(\beta \cdot F \cdot a)}{\beta \cdot F \cdot a} \qquad (20)$$

$$z_{trans} = \exp\left\{\lambda \cdot \Lambda \cdot \left(\frac{2\pi \cdot m}{\beta}\right)^{\frac{3}{2}}\right\} + 2\left[e^{\beta'\kappa} \cosh\{2\beta'(I_1' - 3)\} + 1\right] \qquad (21)$$

These distribution functions are for a localized model as illustrated in FIG. 2, and the following Equation (22) to Equation (24) are obtained when expanded to a macro-model with N molecules.

$$\overline{Z}_{int} = \frac{z_{int}^N}{N!} \qquad (22)$$

$$\overline{Z}_{rot} = \frac{z_{rot}^N}{N!} \qquad (23)$$

$$\overline{Z}_{trans} = \frac{z_{trans}^N}{N!} \qquad (24)$$

Wherein: $\overline{Z}_{int}$ represents a distribution function of intermolecular or intramolecular interaction expanded to N molecules, $\overline{Z}_{rot}$ represents a distribution function of molecular rotation expanded to N molecules, $\overline{Z}_{trans}$ represents a distribution function of molecular translation expanded to N molecules.

The relationships between the distribution functions and the thermodynamic state functions are expressed by the following Equation (25) to Equation (27).

$$U = -\left(\frac{\partial \ln \overline{Z}_{int}}{\partial \beta'}\right)_V \quad (25)$$

$$S = k \cdot \ln\Omega(F) = \ln \overline{Z}_{rot} - \beta \cdot F \cdot a \quad (26)$$

$$pV = \frac{1}{\beta} \cdot \ln \overline{Z}_{trans} \quad (27)$$

Wherein $\beta$ represents $1/RT$. When $T_g$ is the glass transition temperature, then $\beta'$ is expressed by:

$$\frac{1}{R(T-T_g)}$$

n represents a number of links between cross-link points in a statistical molecule chain, and E represents an intermolecular interaction energy coefficient. $\Omega$ (F) represents a state number molecules adopt, with F representing the force generated by a deformed molecule, $\alpha$ represents a statistical molecule length, and k representing the Boltzmann constant. The above Equation (I) is derived by substituting a distribution function for N molecules into these equations. Consequently, a change in Helmholz free energy due to deformation in rubber is expressed as a difference between a non-deformed state and a deformed state.

Each of the terms in above Equation (I) correspond to the respective Equations (II) to (IV) above. Wherein, $I_1'$ considers a local interaction function $\lambda_{micro}$ and is defined by above Equation (V).

In the elastic response performance prediction method of the present exemplary embodiment, the elastic response performance of a rubber product is predicted by employing a constitutive equation expressed by the Equation (I) to Equation (V) derived as described above.

Moreover, in the present exemplary embodiment, the number of links n between cross-linked points in a statistical molecule chain is defined by the following Equation (28), and the temperature dependence is expressed. The temperature and strain dependence can accordingly be considered when applying stress-strain behavior analysis techniques to rubber with extension crystallization properties at the micro-level.

$$n = \alpha \cdot (1 - X_c) \cdot \exp(-\epsilon \cdot \beta) \quad (28)$$

Wherein $\alpha$ represents a frequency factor of statistical segment motion, and $\epsilon$ represents an activation energy of statistical segment motion. $X_c$ represents the crystallization ratio. $X_c$ is represented by the following Equation (29) as a function of internal energy change $\Delta U = U_1 - U_0$ only in cases in which the subject material exhibits extension crystallization properties.

$$X_c = \left(\frac{U_1 - U_0}{\Delta H_0}\right) = \left(\frac{\Delta U}{\Delta H_0}\right) \quad (29)$$

Wherein, $\Delta H$ when crystals melt is equivalent to the entropy of solution. 6 MJ/m$^3$ is employed as $\Delta H$ in cases of natural rubber. Note that $X_c$ is taken as 0 in cases in which the subject material does not exhibit extension crystallization properties. Moreover, $X_c$ is never 1 or greater, since there can never be more than 100% crystallization due to extension.

By appropriate application of Equation (28) and Equation (29), to the Equation (I), an internal energy term U is expressed as a negative value (exothermic) the larger the deformation of rubber with extension crystallization properties. Moreover, in a stretched molecule phenomenon there are limitations to the entropy S by molecular mobility between cross-linked points due to crystallization, and the value of n becomes smaller, and S increases, in proportion to the crystallization ratio. A constitutive equation is accordingly obtained expressing stretched molecules or non-linear behavior in regions where large deformation is observed due to extension crystallization.

Explanation follows regarding operation when prediction of deformation behavior in a rubber material is performed according to the first exemplary embodiment.

First, a 3D-model of a rubber product, such as a tire, is generated by the computer 50, and the 3D-model data is stored on the HDD.

Next, a user operates the input-output terminal to set the 3D-model to be subjected to analysis. The user then operates the input-output terminal to set analysis conditions for analysis processing. The analysis condition setting includes framework conditions of the rubber portion of the 3D-model, and setting framework conditions for filler portions. As framework conditions of the rubber portion of the 3D-model, the constitutive equation of the above Equations (I) to (V) and (28) is set (when the rubber exhibits extension crystallization), or the constitutive equation of Equations (I) to (V) and (29) is set (when the rubber does not exhibit extension crystallization).

The computer 50 then reads in the 3D-model data of the 3D-model set as the subject of analysis from the HDD, and applies the set analysis conditions as the framework conditions of the rubber portion and the filler portion of the 3D-model expressed by the read-in 3D-model data, so as to reconstruct the 3D-model data.

Next, the computer 50 employs the reconstructed 3D-model data to analyze with a finite element method the strain and the internal stress distribution in the 3D-model, and the stress values of the 3D-model as a whole, resulting from vehicle load bearing on the tire, internal pressure of the tire, rolling of the tire etc. when the 3D-model is changed under the framework conditions that have been set.

The computer 50 then displays on a display the strain state and the internal stress distribution of the 3D-model, and the stress values of the 3D-model as a whole, that have been derived by analysis, and then ends processing.

Figure 3:
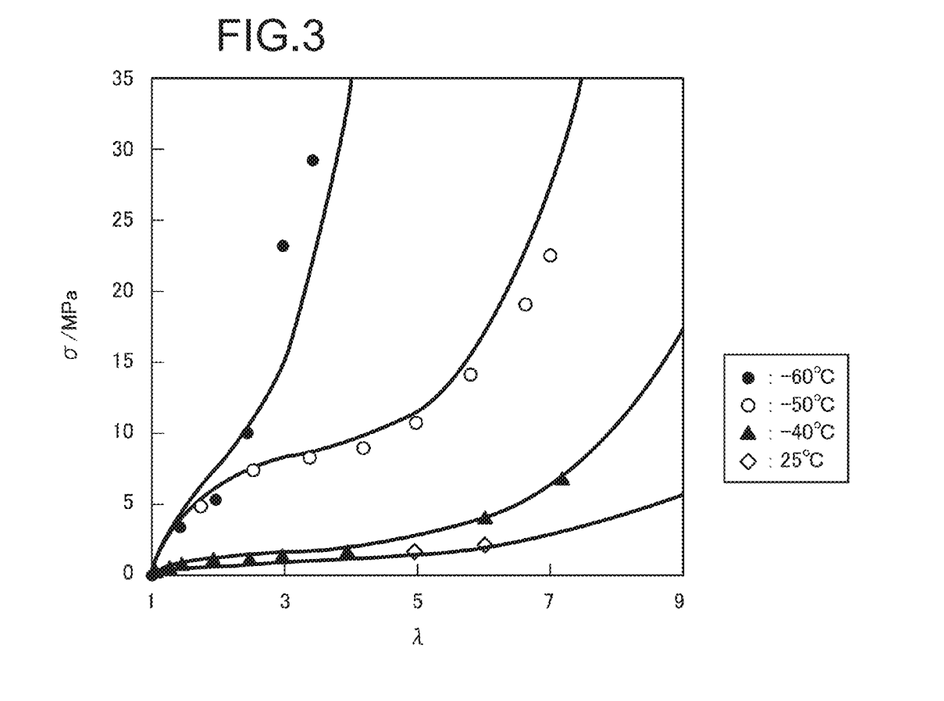
FIG. 3 is a graph illustrating prediction values and observed values related to the temperature dependence of a stress-strain curve of cross-linked styrene butadiene rubber.

Then the constitutive equation described above, this being the Equations (I) to (V), is employed and prediction of the temperature dependence of the stress-strain curve of the rubber is performed, and the temperature dependence of the stress-strain curve is also measured using the cross-linked styrene butadiene rubber. A comparison is then performed between the prediction values (solid line) by the prediction described above, and the measurement values (plots). A comparison result is illustrated in FIG. 3. It can be said that there is a good match shown between the curves obtained with the Equations (I) to (V) and the measurement value plots, particularly in low extension ratio regions.

Figure 4:
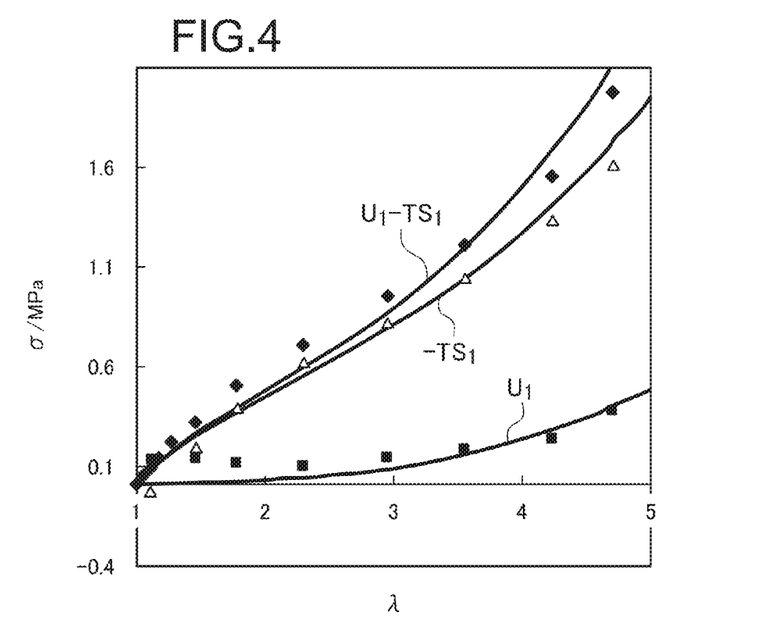
FIG. 4 is a graph illustrating measurement values and computed values related to stress due to energy elasticity and stress due to entropy elasticity of a stress-strain curve at room temperature for a cross-linked styrene butadiene rubber.

Moreover, cross-linked styrene butadiene rubber is employed, measurement of the stress due to energy elasticity and the stress due to entropy elasticity for a stress-strain curve at room temperature is performed, and computation is also performed of the portion ($U_1$-$TS_1$) corresponding to the Equations (I), (II) in the above constitutive equation. A comparison is performed between the above measurement value (plots) and computed values (solid lines). Comparison results are illustrated in FIG. 4. It can be seen that there is a good match between the curves obtained by the portions corresponding to the Equations (I), (II) and the plots of the measurement values.

Figure 5:
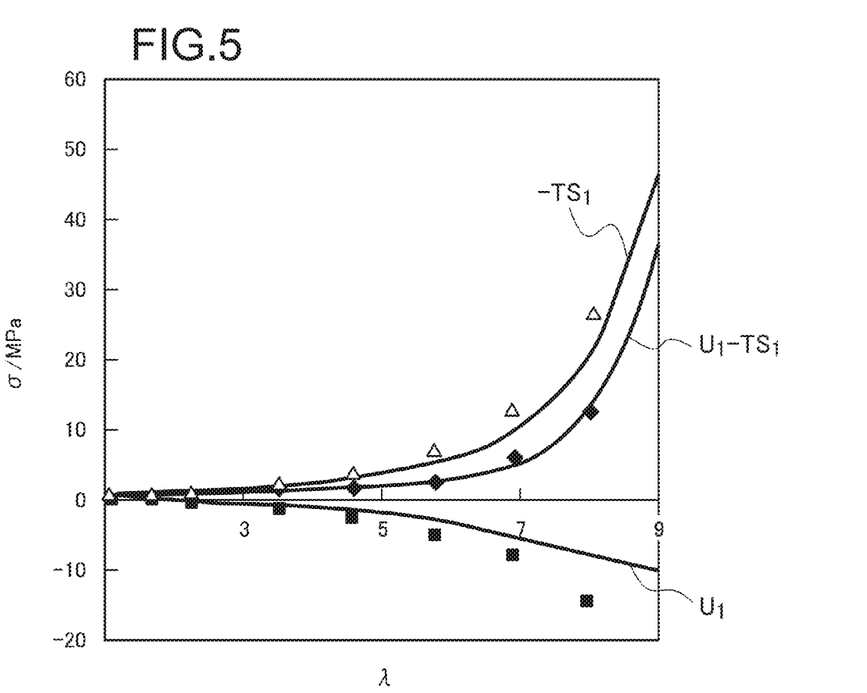
FIG. 5 is a graph illustrating measurement values and computed values related to stress due to energy elasticity and stress due to entropy elasticity of a stress-strain curve at room temperature for a cross-linked natural rubber.

Moreover cross-linked natural rubber is employed, measurement is performed of the stress due to energy elasticity and the stress due to entropy elasticity for a stress-strain curve at room temperature, and the Equations (28) and (29) are also applied and computation performed of the portion ($U_1$-$TS_1$) corresponding to the Equations (I) and (II) in the above constitutive equation. A comparison is made between the above measurement values (plots) and computed values (solid lines). Comparison results are illustrated in FIG. 5. It can be seen that there is a good match between the curves obtained by the portion corresponding to the Equations (I) and (II) and the plots of the measurement values. Since natural rubber exhibits extension crystallization, there is a tendency for the energy elasticity to become minus when the extension ratio is 3 or greater. Since such a phenomenon is also well represented, it can be said that good modeling can also be achieved even for extension crystallization.

As explained above, according to a rubber product elastic response performance prediction apparatus according to the first exemplary embodiment, when a filler based rubber is observed by observation at the micro-level, in a diffuse deformation region of a rubber product, a constitutive equation is employed that expresses temperature and strain dependence of strain energy employing a local interaction function $\lambda_{micro}$ incorporated with the effects of adjacent molecules at low strain, so as to predict the elastic response performance of a rubber product. Accordingly, elastic response performance in low temperature conditions, particularly in a low extension ratio region, can be predicted with good precision.

A microstructure model is defined, and errors in portions of interaction as viewed in micro, in particular the contribution of entropy elasticity in low deformation regions and the phenomenon called extension crystallization, are incorporated, enabling the divergence from observed values to be reduced. The elastic response performance of a rubber product can accordingly be predicted with good precision.

Moreover, a feature is that the energy elasticity is considered in addition to conventional consideration of the contribution of entropy elasticity. The energy elasticity is considered in a similar manner to the strain energy function proposed in Japanese Patent No. 4299735, however a microstructure model thereof was not clearly defined. Hence errors in the portions of interaction as viewed in micro, and in particular the contribution of energy elasticity in low deformation regions, and the phenomenon called extension crystallization where unable to be represented. In the present invention there is a clear microstructure model for statistical thermodynamic computation, and by deriving a constitutive equation based on this model, a universal constitutive equation for rubber elasticity is derived that does not depend on the deformation region or the type of rubber.

With a conventional rubber constitutive equation it was not possible to express the thermodynamic behavior of the rubber, as is illustrated in FIG. 4 and FIG. 5. In the present invention, a constitutive equation expressing the thermodynamic behavior of rubber such as illustrated in FIG. 4 and FIG. 5, is introduced into a conventional computational simulation. It is accordingly possible to perform predictive computation in a state reflecting the thermodynamic behavior of raw materials actually employed.

Moreover, the temperature dependence of a stress-strain curve expressed by employing the constitutive equation obtained from statistical thermodynamic computation has been confirmed to have a good match with results from measurements including those for natural rubber that exhibits extension crystallization properties. Thus by introducing the proposed constitutive equation into a finite element method stress-strain curve, it is possible to represent the rubber stress-strain behavior of rubber at the nanoscale for both rubbers with extension crystallization properties and rubbers without crystallization properties, including elasticity contributions, viscosity contributions, and plasticity contributions therein.

Explanation next follows regarding a second exemplary embodiment.

The second exemplary embodiment differs from the first exemplary embodiment regarding the prediction of elastic response performance of a rubber product in the point that a constitutive equation is employed that expresses the temperature and strain dependence of an elastic modulus of a rubber product.

An elastic response performance prediction method of the second exemplary embodiment is derived similarly to that of the first exemplary embodiment, and a constitutive equation expressed by above Equation (VI) is applied to a deformation behavior analysis technique for rubber at the micro-level to predict the elastic response performance of a rubber product.

Each of the terms in the above Equation (VI) are expressed by the above Equations (VII), (VIII) and (IX). Wherein, $I_1'$ is expressed by employing a local interaction function $\lambda_{micro}$ and is expressed by Equation (X).

In the present exemplary embodiment, the number of links n between cross-linked points in a statistical molecule chain is defined using the above Equations (28) and (29), so as to represent extension crystallization. Thus temperature and strain dependence can be considered even in cases in which a deformation behavior analysis technique is applied at the micro-level to a rubber with extension crystallization properties.

Note that since other configuration and operation of the elastic response performance prediction apparatus according to a second exemplary embodiment of the present invention are similar to those of the first exemplary embodiment, explanation is omitted thereof.

Thus according to the rubber product elastic response performance prediction apparatus according to the second exemplary embodiment, when a filler based rubber is observed by observation at the micro-level, in a diffuse deformation region of a rubber product, a constitutive equation is employed that expresses temperature and strain dependence of an elastic modulus employing a local interaction function $\lambda_{micro}$ incorporated with the effects of adjacent molecules at low strain, so as to predict the elastic response performance of a rubber product. Accordingly, elastic response performance in low temperature conditions, particularly in a low extension ratio region, can be predicted with good precision.

A microstructure model is defined, and errors in portions of interaction as viewed in micro, in particular the contribution of entropy elasticity in low deformation regions and the phenomenon of extension crystallization, are incorporated, enabling the divergence from observed values to be reduced. The elastic response performance of a rubber product can accordingly be predicted with good precision.

The entire contents disclosed in Japanese Patent Application No. 2010-225985 is incorporated by reference into the present specification.

All cited documents, patent applications and technical standards mentioned in the present specification are incorporated by reference in the present specification to the same extent as if the individual cited document, patent application, or technical standard was specifically and individually indicated to be incorporated by reference.

The invention claimed is:

1. An elastic response performance prediction method, performed on an elastic response performance prediction apparatus, that predicts an elastic response performance expressing deformation behavior of a rubber product, the elastic response performance prediction method comprising:

generating a model of the rubber product by a computer and storing said model thereon, operating an input-output terminal to set a constitutive equation as a framework condition of the rubber product, applying the framework condition to the model of the rubber product, and reconstructing model data of the model, deforming the model under the framework conditions and predicting the elastic response performance of the rubber product by employing the constitutive equation that expresses temperature and strain dependence of strain energy in the rubber product expressed using a parameter representing intermolecular interaction, generating a reconstructed model based on the operating, applying, and deforming steps, analyzing a strain state and a stress distribution of the reconstructed model, and displaying on a display the strain state and a stress distribution of the reconstructed model, wherein the constitutive equation is the following Equation (I):

$$\Delta A = (U_1 - TS_1) + p(V_1 - V_0) - (U_0 - TS_0) \quad \text{(I)}$$

wherein A represents Helmholz free energy, $U_0$ represents internal energy in a non-deformed state, $U_1$ represents internal energy in a deformed state, p represents pressure, $V_0$ represents volume in a non-deformed state, $V_1$ represents volume in a deformed state, T represents absolute temperature, $S_0$ represents entropy in a non-deformed state, and $S_1$ represents entropy in a deformed state, with each of the terms of Equation (I) expressed by the following Equations (II) to (IV):

$$U_1 - T \cdot S_1 = \frac{e^{\beta' \kappa} \{\kappa \cosh(2\beta'(I_1' - 3)) + 2(I_1' - 3) \cdot \sinh(2\beta'(I_1' - 3))\}}{e^{\beta' \kappa} \cosh(2\beta'(I_1' - 3)) + 1} - \frac{N}{\beta} \cdot \left\{ \frac{1}{2} I_1 + \frac{3}{100n}(3I_1^2 - 4I_2) + \frac{99}{12250n}(5I_1^3 - 12I_1 I_2) \right\} \quad \text{(II)}$$

$$p(V_1 - V_0) = B \cdot (V_1 - V_0) = B \left( I_3^{\frac{1}{2}} - 1 \right)^3 - \frac{1}{\beta'} \{\ln[1 + e^{\beta' \kappa} \cosh(2\beta'(I_1' - 3))] - \ln[1 + e^{\beta' \kappa}]\} \quad \text{(III)}$$

$$U_0 - T \cdot S_0 = \frac{\kappa \cdot e^{\beta' \kappa}}{e^{\beta' \kappa} + 1} + \frac{N}{\beta} \left( \frac{3}{2} + \frac{45}{100n} + \frac{2673}{12250n^2} \right) \quad \text{(IV)}$$

wherein: $I_1$, $I_2$, and $I_3$ are expressed as functions of three extension ratios of deformation $\lambda_1$, $\lambda_2$ and $\lambda_3$ in xyz directions in three dimensional axes of rubber by $I_1 = \lambda_1^2 + \lambda_2^2 + \lambda_3^2$, $I_2 = \lambda_1^2 \cdot \lambda_2^2 + \lambda_2^2 \cdot \lambda_3^2 + \lambda_3^2 \cdot \lambda_1^2$, and $I_3 = \lambda_1^2 \cdot \lambda_2^2 \cdot \lambda_3^2$; n represents a number of links between cross-linked points in a statistical molecule chain; κ expresses an intermolecular interaction energy coefficient; $\beta = 1/RT$ and $\beta' = 1/R(T-T_g)$ wherein R is a gas constant and $T_g$ is a glass transition temperature; and $I_1'$ is expressed using a local interaction function $\lambda_{micro}$ as a parameter expressing the intermolecular interaction by the following Equation (V):

$$I_1' = \lambda_{micro}^2 (\lambda_1^2 + \lambda_2^2 + \lambda_3^2) = \lambda_{micro}^2 I_1 \quad \text{(V)}$$

2. An elastic response performance prediction method, performed on an elastic response performance prediction apparatus, that predicts elastic response performance expressing deformation behavior of a rubber product, the elastic response performance prediction method comprising:

generating a model of the rubber product by a computer and storing said model thereon, operating an input-output terminal to set a constitutive equation as a framework condition of the rubber product, applying the framework condition to the model of the rubber product, and reconstructing model data of the model, deforming the model under the framework conditions and predicting the elastic response performance of the rubber product by employing the constitutive equation that expresses temperature and strain dependence of strain energy in the rubber product expressed using a parameter representing intermolecular interaction, generating a reconstructed model based on the operating, applying, and deforming steps, analyzing a strain state and a stress distribution of the reconstructed model, and displaying on a display the strain state and a stress distribution of the reconstructed model, wherein the constitutive equation is the following Equation (VI):

$$G = \frac{\partial W}{\partial I_1} = \frac{\partial A}{\partial I_1} = \frac{\partial U}{\partial I_1} - T \cdot \frac{\partial S}{\partial I_1} + \frac{\partial pV}{\partial I_1} \quad \text{(VI)}$$

wherein G represents a shear elastic modulus, W represents a strain energy coefficient, A represents Helmholz free energy, U represents internal energy, T represents absolute temperature, S represents entropy, and $I_1$, is expressed as a function of three extension ratios of deformation $\lambda_1$, $\lambda_2$ and $\lambda_3$ in xyz directions in three dimensional axes of rubber by $I_1 = \lambda_1^2 + \lambda_2^2 + \lambda_3^2$, with each of the terms of Equation (VI) respectively expressed by the following Equation (VII), Equation (VIII), and Equation (IX):

$$\frac{\partial U}{\partial I_1} = \frac{-e^{\beta' \kappa} \left\{ \begin{array}{l} e^{\beta' \kappa} \sinh(2\beta'(I_1' - 3)) \cosh(2\beta'(I_1' - 3)) + \\ 2(\beta' x + I) \sinh(2\beta'(I_1' - 3)) + \\ 4\beta'(I_1' - 3) \cosh(2\beta'(I_1' - 3)) + \\ 4\beta'(I_1' - 3) e^{\beta' \kappa} \end{array} \right\}}{\{e^{\beta' \kappa} \cdot \cosh(2\beta'(I_1' - 3)) + 1\}^2} \quad \text{(VII)}$$

$$\frac{\partial S}{\partial I_1} = -vR \left[ \frac{1}{2} + \frac{3}{50n} \left( 3I_1 - \frac{2}{\lambda} \right) + \frac{297}{6125n^2} \left( 5I_1^2 - 4I_2 - 4\frac{I_1}{\lambda} \right) \right] \quad \text{(VIII)}$$

$$\frac{\partial pV}{\partial I_1} = \frac{2 \cdot e^{\beta' \kappa} \cdot \cosh(2\beta'(I_1' - 3))}{e^{\beta' \kappa} \cdot \cosh(2\beta'(I_1' - 3)) + 1} \quad \text{(IX)}$$

wherein n represents a number of links between cross-linked points in a statistical molecule chain; κ expresses an intermolecular interaction energy coefficient; v represents a cross-link density; λ represents an extension ratio or compression ratio; $\beta' = 1/R(T-T_g)$ wherein R is a gas constant and $T_g$ is a glass transition temperature; $I_2$ is represented by $I_2=\lambda_1^2 \cdot \lambda_2^2+\lambda_2^2 \cdot \lambda_3^2+\lambda_3^2 \cdot \lambda_1^2$; and $I_1'$ is expressed using a local interaction function $\lambda_{micro}$ as a parameter expressing the intermolecular interaction by the following Equation (X):

$$I_1'=\lambda_{micro}^2(\lambda_1^2+\lambda_2^2+\lambda_3^2)=\lambda_{micro}^2 I_1 \quad (X).$$

3. The elastic response performance prediction method of claim 1, wherein the elastic response performance expressing deformation behavior of the rubber product is predicted using a finite element analysis method.

4. A rubber product design method comprising designing a rubber product by employing the elastic response performance prediction method of claim 1.

5. An elastic response performance prediction apparatus, performed on an elastic response performance prediction apparatus, that predicts elastic response performance expressing deformation behavior of a rubber product, the elastic response performance prediction apparatus predicting the elastic response performance of the rubber product by:
   generating a model of the rubber product by a computer and storing said model thereon,
   operating an input-output terminal to set a constitutive equation as a framework condition of the rubber product,
   applying the framework condition to the model of the rubber product, and reconstructing model data of the model,
   deforming the model under the framework conditions and employing the constitutive equation that expresses temperature and strain dependence of strain energy in the rubber product expressed using a parameter representing intermolecular interaction,
   generating a reconstructed model based on the operating, applying, and deforming steps,
   analyzing a strain state and a stress distribution of the reconstructed model, and
   displaying on a display the strain state and a stress distribution of the reconstructed model,
   wherein the constitutive equation is the following Equation (I):

$$\Delta A=(U_1-TS_1)+p(V_1-V_0)-(U_0-TS_0) \quad (I)$$

wherein A represents Helmholz free energy, $U_0$ represents internal energy in a non-deformed state, $U_1$ represents internal energy in a deformed state, p represents pressure, $V_0$ represents volume in a non-deformed state, $V_1$ represents volume in a deformed state, T represents absolute temperature, $S_0$ represents entropy in a non-deformed state, and $S_1$ represents entropy in a deformed state, with each of the terms of Equation (I) expressed by the following Equations (II) to (IV):

$$U_1-T \cdot S_1 = \frac{e^{\beta' \kappa}\{\kappa \cosh(2\beta'(I_1'-3))+2(I_1'-3)\cdot \sinh(2\beta'(I_1'-3))\}}{e^{\beta'\kappa}\cosh(2\beta'(I_1'-3))+I} - \frac{N}{\beta} \cdot \left\{ \frac{1}{2}I_1 + \frac{3}{100n}(3I_1^2-4I_2) + \frac{99}{12250n}(5I_1^3-12I_1 I_2) \right\} \quad (II)$$

$$p(V_1-V_0)=B \cdot (V_1-V_0)= B\left(I_3^{\frac{1}{2}}-1\right)^2 - \frac{1}{\beta'}\{\ln[1+e^{\beta' \kappa}\cosh(2\beta'(I_1'-3))]-\ln[1+e^{\beta' \kappa}]\} \quad (III)$$

$$U_0-T \cdot S_0 = \frac{\kappa \cdot e^{\beta' \kappa}}{e^{\beta' \kappa}+1} + \frac{N}{\beta}\left(\frac{3}{2}+\frac{45}{100n}+\frac{2673}{12250n^2}\right) \quad (IV)$$

wherein: $I_1$, $I_2$, and $I_3$ are expressed as functions of three extension ratios of deformation $\lambda_1$, $\lambda_2$ and $\lambda_3$ in xyz directions in three dimensional axes of rubber by $I_1=\lambda_1^2+\lambda_2^2+\lambda_3^2$, $I_2=\lambda_1^2 \cdot \lambda_2^2+\lambda_2^2 \cdot \lambda_3^2+\lambda_3^2 \cdot \lambda_1^2$, and $I_3=\lambda_1^2 \cdot \lambda_2^2 \cdot \lambda_3^2$; n represents a number of links between cross-linked points in a statistical molecule chain; $\kappa$ expresses an intermolecular interaction energy coefficient; $\beta=1/RT$ and $\beta'=1/R$ $(T-T_g)$ wherein R is a gas constant and $T_g$ is a glass transition temperature; and $I_1'$ is expressed using a local interaction function $\lambda_{micro}$ as a parameter expressing the intermolecular interaction by the following Equation (V):

$$I_1'=\lambda_{micro}^2(\lambda_1^2+\lambda_2^2+\lambda_3^2)=\lambda_{micro}^2 I_1 \quad (V).$$

6. An elastic response performance prediction apparatus, performed on an elastic response performance prediction apparatus, that predicts elastic response performance expressing deformation behavior of a rubber product, the elastic response performance prediction apparatus predicting the elastic response performance of the rubber product by:
   generating a model of the rubber product by a computer and storing said model thereon,
   operating an input-output terminal to set a constitutive equation as a framework condition of the rubber product,
   applying the framework condition to the model of the rubber product, and reconstructing model data of the model,
   deforming the model under the framework conditions and employing the constitutive equation that expresses temperature and strain dependence of strain energy in the rubber product expressed using a parameter representing intermolecular interaction,
   generating a reconstructed model based on the operating, applying, and deforming steps,
   analyzing a strain state and a stress distribution of the reconstructed model, and
   displaying on a display the strain state and a stress distribution of the reconstructed model,
   wherein the constitutive equation is the following Equation (VI):

$$G=\frac{\partial W}{\partial I_1}=\frac{\partial A}{\partial I_1}=\frac{\partial U}{\partial I_1}-T \cdot \frac{\partial S}{\partial I_1}+\frac{\partial pV}{\partial I_1} \quad (VI)$$

wherein G represents a shear elastic modulus, W represents a strain energy coefficient, A represents Helmholz free energy, U represents internal energy, T represents absolute temperature, S represents entropy, and $I_1$, is expressed as a function of three extension ratios of deformation $\lambda_1$, $\lambda_2$ and $\lambda_3$ in xyz directions in three dimensional axes of rubber by $I_1=\lambda_1^2+\lambda_2^2+\lambda_3^2$, with each of the terms of Equation (VI) respectively expressed by the following Equation (VII), Equation (VIII), and Equation (IX):

$$\frac{\partial U}{\partial I_1}=\frac{-e^{\beta' \kappa}\{2e^{\beta' \kappa}\sinh(2\beta'(I_1'-3))\cosh(2\beta'(I_1'-3))+2(\beta'\kappa+1)\sinh(2\beta'(I_1'-3))+4\beta'(I_1'-3)\cosh(2\beta'(I_1'-3))+4\beta'(I_1'-3)e^{\beta' \kappa}\}}{\{e^{\beta' \kappa} \cdot \cosh(2\beta'(I_1'-3))+1\}^2} \quad (VII)$$

$$\frac{\partial S}{\partial I_1}=-vR\left[\frac{1}{2}+\frac{3}{50n}\left(3I_1-\frac{2}{\lambda}\right)+\frac{297}{6125n^2}\left(5I_1^2-4I_2-4\frac{I_1}{\lambda}\right)\right] \quad (VIII)$$

-continued $$\frac{\partial pV}{\partial I_1} = \frac{2 \cdot e^{\beta'\kappa} \cdot \cosh(2\beta'(I_1'-3))}{e^{\beta'\kappa} \cdot \cosh(2\beta'(I_1'-3))+1} \quad (IX)$$

wherein n represents a number of links between cross-linked points in a statistical molecule chain; κ expresses an intermolecular interaction energy coefficient; ν represents a cross-link density; λ represents an extension ratio or compression ratio; $\beta'=1/R\,(T-T_g)$ wherein R is a gas constant and $T_g$ is a glass transition temperature; $I_2$ is represented by $I_2 = \lambda_1^2 \cdot \lambda_2^2 + \lambda_2^2 \cdot \lambda_3^2 + \lambda_3^2 \cdot \lambda_1^2$; and $I_1'$ is expressed using a local interaction function $\lambda_{micro}$ as a parameter expressing the intermolecular interaction by the following Equation (X):

$$I_1' = \lambda_{micro}^2(\lambda_1^2 + \lambda_2^2 + \lambda_3^2) = \lambda_{micro}^2 I_1 \quad (X).$$

* * * * *